United States Patent
Charlton

(10) Patent No.: US 8,191,396 B2
(45) Date of Patent: Jun. 5, 2012

(54) TEST-SENSOR PACKAGING

(75) Inventor: Steven C. Charlton, Osceola, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 709 days.

(21) Appl. No.: 12/226,852

(22) PCT Filed: May 3, 2007

(86) PCT No.: PCT/US2007/010606
§ 371 (c)(1),
(2), (4) Date: Oct. 29, 2008

(87) PCT Pub. No.: WO2007/133455
PCT Pub. Date: Nov. 22, 2007

(65) Prior Publication Data
US 2009/0178470 A1  Jul. 16, 2009

Related U.S. Application Data

(60) Provisional application No. 60/798,538, filed on May 8, 2006.

(51) Int. Cl.
*G01N 21/00* (2006.01)
(52) U.S. Cl. ........................................ 73/1.02
(58) Field of Classification Search .................. None
See application file for complete search history.

(56) References Cited

U.S. PATENT DOCUMENTS

| 5,108,889 A | 4/1992 | Smith ............................... 435/4 |
| 5,556,533 A | 9/1996 | Nozoe et al. ................. 205/777.5 |
| 5,575,403 A | 11/1996 | Charlton et al. ................. 221/31 |
| 5,854,074 A * | 12/1998 | Charlton et al. ................. 436/46 |
| 6,495,104 B1 | 12/2002 | Unno et al. ................... 422/68.1 |
| 6,531,040 B2 | 3/2003 | Musho et al. ................. 204/401 |
| 2003/0032190 A1 | 2/2003 | Brown et al. .................... 436/46 |

FOREIGN PATENT DOCUMENTS

| WO | WO 01/14064 A1 | 3/2001 |
| WO | WO 2006/002432 A1 | 1/2006 |

OTHER PUBLICATIONS

Written Opinion corresponding to International Patent Application No. PCT/US2007/010606, European Patent Office, dated Sep. 8, 2008, 10 pages.
International Search Report corresponding to International Patent Application No. PCT/US2007/010606, European Patent Office, dated Sep. 8, 2008, 4 pages.

* cited by examiner

*Primary Examiner* — Hezron E Williams
*Assistant Examiner* — Alex Devito
(74) *Attorney, Agent, or Firm* — Nixon Peabody LLP

(57) ABSTRACT

A test-sensor cartridge is disclosed. The test-sensor cartridge comprises a plurality of test sensors adapted to assist in determining an analyte concentration of a fluid sample. The test-sensor cartridge further comprises a plurality of walls forming at least one cavity therein, the at least one cavity being adapted to contain the plurality of test sensors. The test-sensor cartridge further comprises at least one opening formed on a surface of the cartridge. The at least one opening is adapted to receive each of at least one projection of a first sensor-dispensing instrument with which the cartridge is compatible. The at least one opening is adapted to receive at least one but less than all of at least one projection of a second sensor-dispensing instrument with which the cartridge is incompatible.

20 Claims, 9 Drawing Sheets

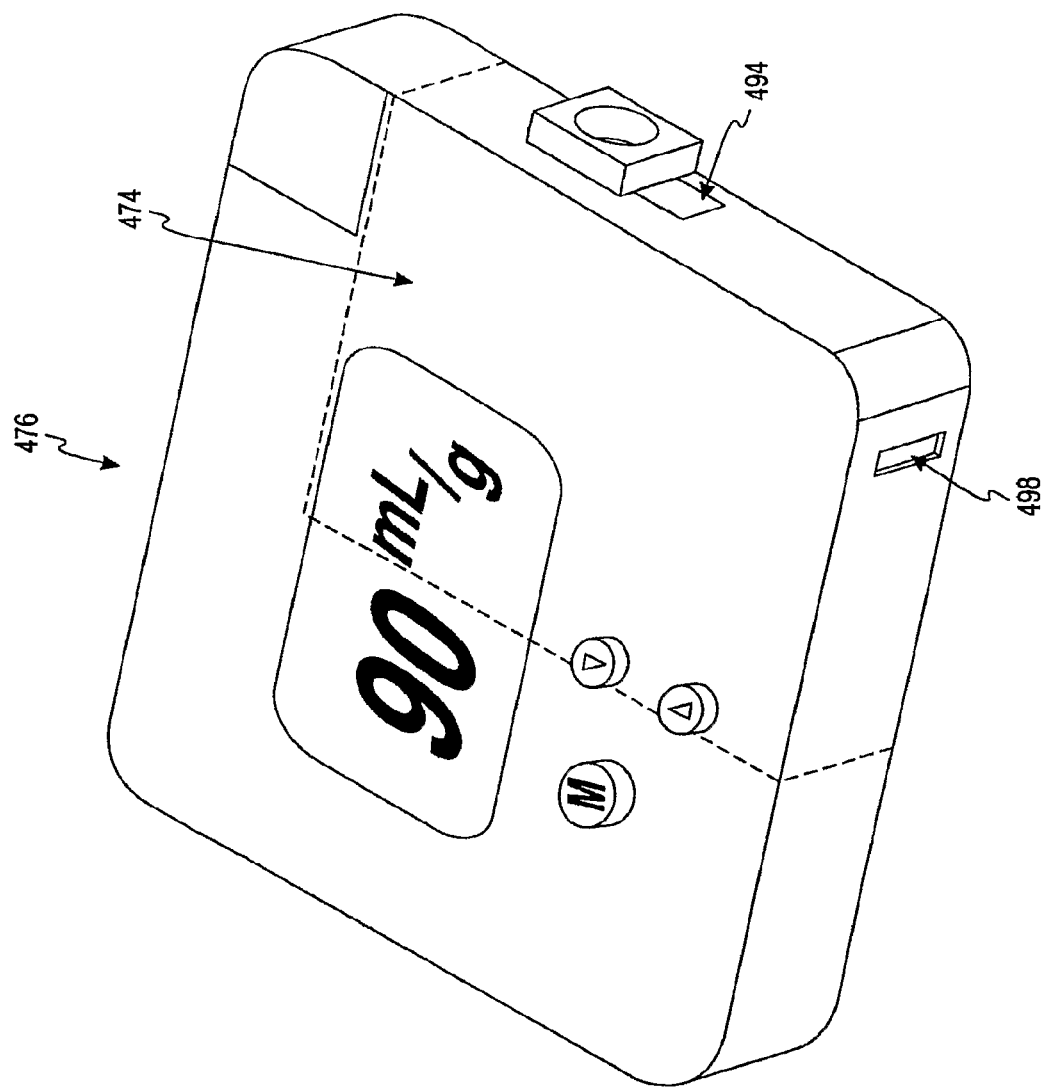

TEST-SENSOR PACKAGING

CROSS-REFERENCE TO RELATED APPLICATIONS

This application claims priority to Application Nos. 60/798,538 filed on May 8, 2006, which is incorporated by reference in its entirety.

FIELD OF THE INVENTION

The present invention relates generally to sensor-dispensing instruments and, more particularly, to test-sensor packaging for limiting the interchangeability of test sensors between different types and/or generations of analyte-testing instruments (e.g., meters).

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. The results of such tests may be used to determine what, if any, insulin and/or other medication needs to be administered. In one type of testing system, test sensors are used to test a fluid such as a sample of blood.

One method of monitoring an individual's blood glucose level is with a portable, hand-held blood glucose testing device (e.g., a meter). To determine the blood glucose level with the meter, a lancet device may be used with a needle lancet that pierces the skin tissue and allows a whole blood sample to form on the skin's surface. Once the requisite amount of blood forms on the skin's surface, the blood sample is transferred to a test sensor. The test sensor is generally placed in an opening in the body of the meter.

Test-sensor cartridges are commonly used to individually dispense test sensors to be used for testing an analyte in a fluid. The cartridges may be incorporated directly into, for example, glucose meters to dispense test sensors for use with the meter. The cartridges are used to store multiple sensors and allow users to carry multiple sensors around within a single enclosure. Test-sensor cartridges may include features designed to mate with corresponding features of a meter to assist in indexing and/or excising the test sensors located within the cartridges. The cartridges also assist in preventing or inhibiting the sensors from being exposed to the environment until they are required for use. During testing, a blood or body fluid sample may be placed on the sensor and analyzed with the meter or instrument to determine the concentration of the analyte being examined.

Because different types of test sensors or test sensor versions may have significant differences associated therewith, a problem occurs when a test sensor is used with a meter that was not designed to be used with the test sensor. This may occur, for example, when a user places a test-sensor cartridge into a meter that is not compatible with the test sensors located within the test-sensor cartridge. Different types of test sensors may include different types of sensor reagent, which may influence items such as the amount of fluid sample needed and the length of time needed to react with the analyte to determine the analyte concentration. Furthermore, different test sensors may correspond with different assay protocols or programs including test sequences, test times, algorithms, voltage, calibration information, or the like.

It may be difficult for a user to determine when a test-sensor cartridge is compatible with a given meter. This difficulty is amplified by the fact that many cartridges are of a generally universal size and configuration and, thus, fit into various types and/or generations of meters. Moreover, meters are generally designed to perform protocols and run programs associated with certain test sensors. Thus, mismatching test-sensor cartridges and meters generally yields inaccurate test results and may result in extra testing, which may be inconvenient and expensive for a user.

It would be desirable to provide test-sensor packaging for limiting the interchangeability of test sensors with different types and/or generations of sensor-dispensing instruments.

SUMMARY OF THE INVENTION

According to one embodiment of the present invention, a test-sensor cartridge is disclosed. The test-sensor cartridge comprises a plurality of test sensors adapted to assist in determining an analyte concentration of a fluid sample. The test-sensor cartridge further comprises a plurality of walls forming at least one cavity therein, the at least one cavity being adapted to contain the plurality of test sensors. The test-sensor cartridge further comprises at least one opening formed on a surface of the cartridge. The at least one opening is adapted to receive each of at least one projection of a first sensor-dispensing instrument with which the cartridge is compatible. The at least one opening is adapted to receive at least one but less than all of at least one projection of a second sensor-dispensing instrument with which the cartridge is incompatible.

According to another embodiment of the present invention, a test-sensor cartridge is disclosed. The test-sensor cartridge comprises a plurality of test sensors adapted to assist in determining an analyte concentration of a fluid sample. The test-sensor cartridge further comprises a plurality of walls forming at least one cavity therein, the at least one cavity being adapted to contain the plurality of test sensors. The test-sensor cartridge further comprises at least one projection formed on a surface of the cartridge. Each of the at least one projection is adapted to be received by at least one opening of a first sensor-dispensing instrument with which the cartridge is compatible. At least one but less than all of the at least one projection is adapted to be received by at least one opening of a second sensor-dispensing instrument with which the cartridge is incompatible.

According to another embodiment of the present invention, a method of determining whether a test-sensor cartridge is compatible with a sensor-dispensing instrument is disclosed. The method comprises the act of providing a test-sensor cartridge including a plurality of walls forming at least one cavity therein. The at least one cavity is adapted to contain a plurality of test sensors. The plurality of test sensors is adapted to assist in the determination of a concentration of an analyte in a fluid sample. The test-sensor cartridge has at least one opening formed on at least one of the plurality of walls. The method further comprises providing a sensor-dispensing instrument having at least one projection located therein. The method further comprises inserting the test-sensor cartridge into the sensor-dispensing instrument. The method further comprises determining whether the test-sensor cartridge is compatible with the sensor-dispensing instrument based on whether the at least one opening is adapted to receive each of the at least one projection.

According to another embodiment of the present invention, a method of determining whether a test-sensor cartridge is compatible with a sensor-dispensing instrument is disclosed. The method comprises the acts of providing a test-sensor cartridge including a plurality of walls forming at least one cavity therein. The at least one cavity is adapted to contain a plurality of test sensors. The plurality of test sensors is adapted to assist in the determination of a concentration of an analyte in a fluid sample. The test-sensor cartridge has at least one projection formed on at least one of the plurality of walls. The method further comprises providing a sensor-dispensing instrument having at least one opening located therein. The method further comprises inserting the test-sensor cartridge into the sensor-dispensing instrument. The method further comprises determining whether the test-sensor cartridge is compatible with the sensor-dispensing instrument based on whether the at least one opening is adapted to receive each of the at least one projection.

According to another embodiment of the present invention, a test-sensor cartridge is disclosed. The test-sensor cartridge comprises a plurality of walls forming at least one cavity therein. The at least one cavity is adapted to contain a plurality of test sensors. The plurality of test sensors is adapted to assist in the determination of a concentration of an analyte in a fluid sample. The test-sensor cartridge further comprises at least one opening formed on a surface of the cartridge. The at least one opening assists in indexing the test-sensor cartridge. When the test-sensor cartridge is indexed within a first sensor-dispensing instrument with which the cartridge is compatible, a test-sensor cavity is aligned with an ejection mechanism. When the test-sensor cartridge is indexed within a second sensor-dispensing instrument with which the cartridge is incompatible, a test-sensor cavity is not aligned with an ejection mechanism.

The above summary of the present invention is not intended to represent each embodiment or every aspect of the present invention. Additional features and benefits of the present invention are apparent from the detailed description and figures set forth below.

BRIEF DESCRIPTION OF THE DRAWINGS

FIG. 7b is a perspective view of a meter to which the ejection mechanism of FIG. 7a is attached internally and being used with the stacked test-sensor cartridge of FIG. 7a.

Figure 1:
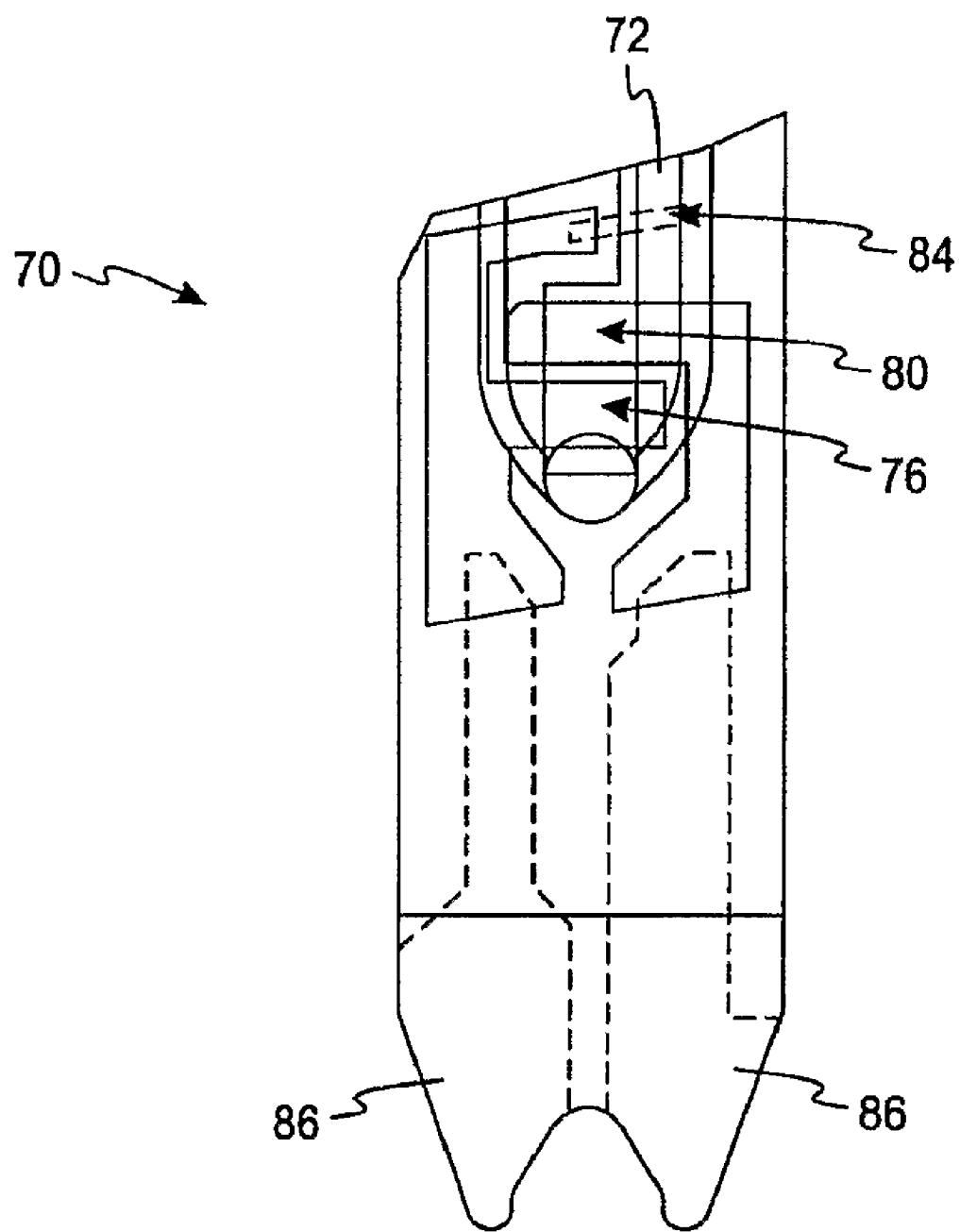
FIG. 1 is a top view of a test sensor according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATED EMBODIMENTS

The present invention is directed to limiting the interchangeability of a test-sensor cartridge between various types and/or generations of sensor-dispensing instruments (e.g., meters). The test sensors (e.g., biosensors) excised from the cartridge may be used to assist in determining an analyte concentration in a fluid sample. Some examples of the types of analytes that may be collected and analyzed include glucose, lipid profiles (e.g., cholesterol, triglycerides, LDL, and HDL), microalbumin, fructose, lactate, or bilirubin. The present invention is not limited, however, to these specific analytes, and it is contemplated that other analyte concentrations may be determined. The analytes may be in, for example, a whole blood sample, a blood serum sample, a blood plasma sample, or other body fluids like ISF (interstitial fluid) and/or urine. One non-limiting example of a use of the test-sensor cartridge and meter is to determine the glucose concentration in a user's blood, plasma, or ISF.

Test sensors used in determining analyte concentrations are typically provided with a capillary channel that extends from the front or testing end of the test sensor to biosensing or reagent material disposed in the test sensor. The reagent generally includes an appropriately selected enzyme to react with the desired analyte or analytes to be tested. The reagent may be stored within the test sensor in a dried ink form to promote an extended shelf life of the test sensor. When the testing end of the test sensor is placed into fluid (e.g., blood that is accumulated on a person's finger after the finger has been pricked), a portion of the fluid is drawn into the capillary channel by capillary action. The fluid then mixes with the reagent material in the test sensor and chemically reacts with the reagent material so that an electrical signal indicative of the analyte (e.g., glucose) level in the fluid being tested is supplied and subsequently transmitted to a sensor-dispensing instrument or meter.

One type of test sensor that may be used is an electrochemical test sensor. One non-limiting example of an electrochemical test sensor is shown in FIG. 1. FIG. 1 depicts a test sensor 70 that includes a capillary channel 72, an area for meter contacts 86, and a plurality of electrodes 76, 80, 84. The capillary channel 72 contains reagent. The plurality of electrodes includes a working (measuring) electrode 80, a counter electrode 76, and an optional trigger electrode 84. The trigger electrode 84 may assist in determining whether a sufficient blood sample has been placed on the sensor 70. The electrochemical test sensor may also contain other amounts and/or types of electrodes. Examples of electrochemical test sensors, including their operation, may be found in, for example, U.S. Pat. No. 6,531,040 assigned to Bayer Corporation. It is contemplated that other electrochemical test sensors may be employed. It is also contemplated that other types of test sensors may be used including, but not limited to, optical test sensors.

Figure 2:
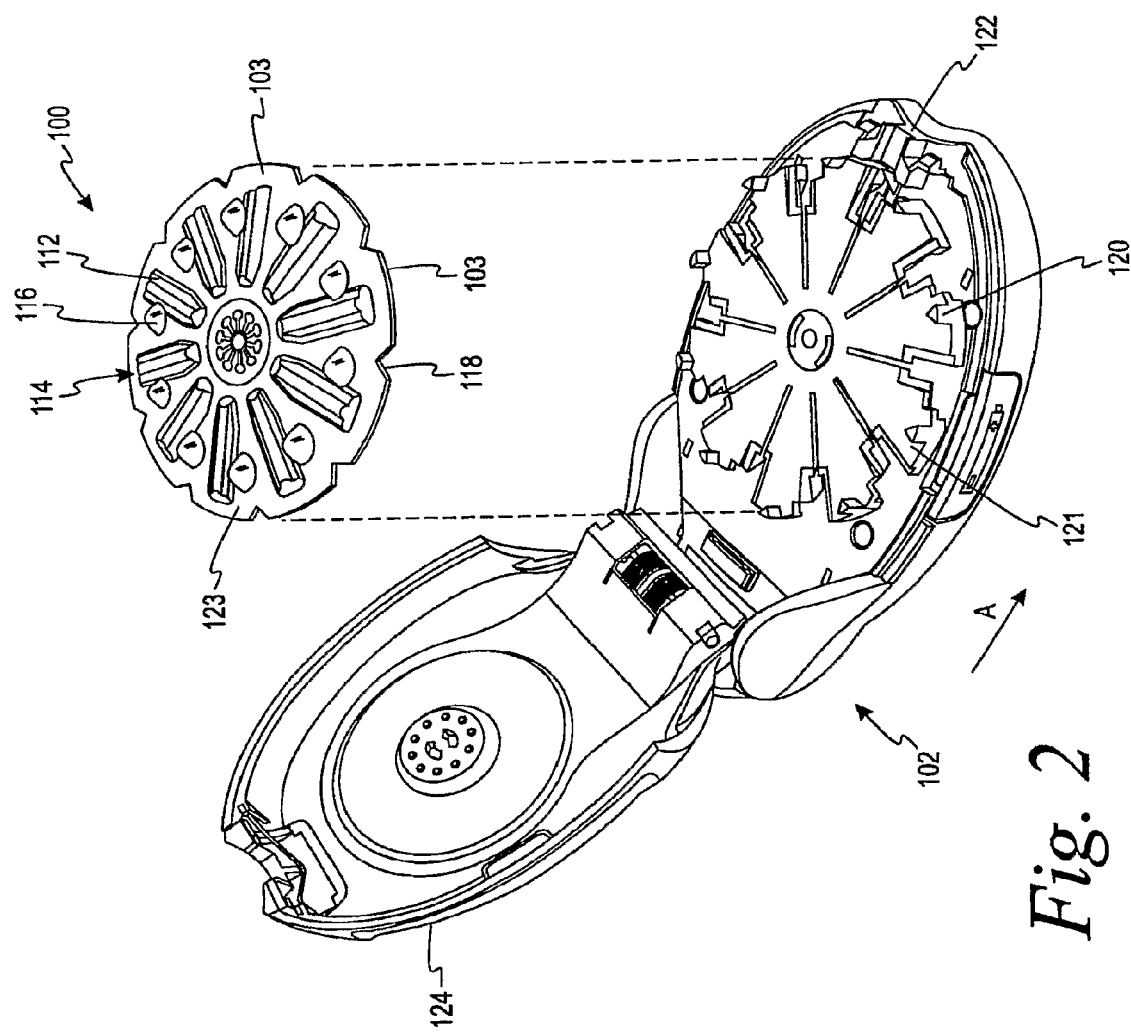
FIG. 2 is a perspective view of a sensor-dispensing instrument or meter in an open position showing a test-sensor cartridge being inserted according to one embodiment.
Figure 3A:
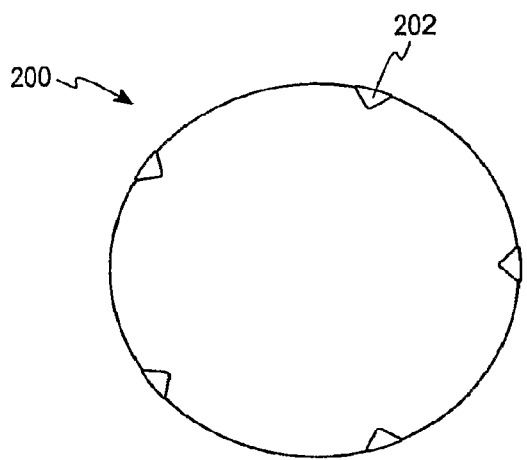
FIGS. 3a-d illustrate top, representative views of indexing mechanisms having various post layouts.
Figure 3B:
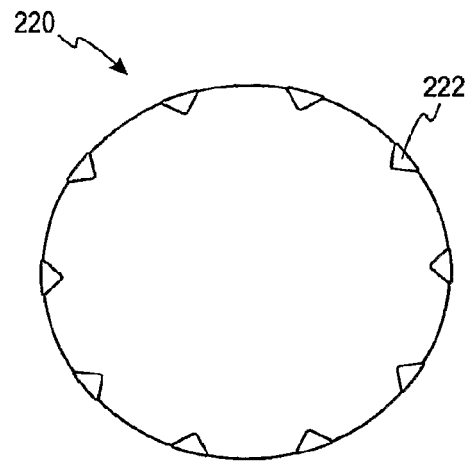
Figure 3C:
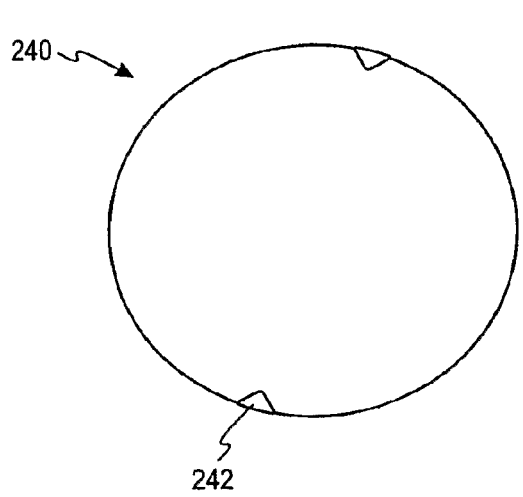
Figure 3D:
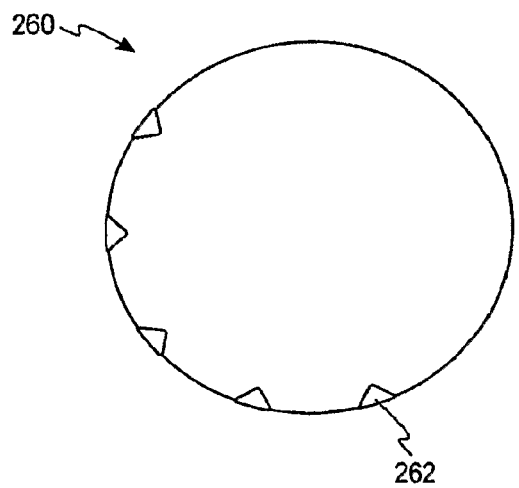

A plurality of test sensors is typically stored in a disposable test-sensor cartridge. For example, the plurality of test sensors may be stored in a cartridge where the test sensors are generally radially aligned and individually packaged in sensor cavities (e.g., a blister-type pack). An example of a disposable cartridge 100 being placed in a sensor-dispensing instrument or meter 102 is depicted in FIG. 2. The disposable cartridge 100 is an example of a blister-type pack. The cartridge 100 includes a generally flat surface 103 having a plurality of walls forming a plurality of test-sensor cavities 114 therein. A plurality of test sensors 112 is individually stored in a respective one of the plurality of sensor cavities 114. The cartridge 100 further includes at least one desiccant compartment 116 for maintaining the test sensors 112 at adequate moisture levels such that accurate testing may be achieved. The disposable cartridge 100 of FIG. 2 is further described at U.S. Patent Application Publication No. 2003/0032190 that published on Feb. 13, 2003 and is entitled "Mechanical Mechanism for a Blood Glucose Sensor-Dispensing Instrument." It is contemplated that other types of blister-type packs and other types of cartridges may also be used.

The cartridge 100 of FIG. 2 further includes a plurality of openings. Although in the illustrated embodiments, the openings include notches positioned along the periphery of the generally flat surface 103, it is contemplated that other types of openings located along other suitable portions of the cartridge 100 may also be used with the present invention. It is also contemplated that the openings may have shapes other than those of the illustrated embodiments. For example, the openings may be in the form of one or more notches formed along the periphery of the cartridge 100, one or more apertures formed a certain distance from the periphery, or the like. It is further contemplated that the notches referred to herein may have any shape including, but not limited to, the V-shape of the illustrated embodiments.

Referring back to the embodiment of FIG. 2, the plurality of openings include a plurality of notches 118 adapted to receive a corresponding one of a plurality of projections, or posts 120, positioned on an indexing mechanism 121 within the meter 102. It is contemplated that projections other than the posts 120 shown in the illustrated embodiments may also be used with the present invention. In the embodiment of FIG. 2, the indexing mechanism 121 is in the form of a wheel and the posts 120 are arranged along the periphery of the wheel. It is contemplated, however, that other types of indexing mechanisms may be used with the present invention. The number of notches 118 in the illustrated embodiment corresponds with the number of posts 120 (i.e., ten). To insert the cartridge 100 into the meter 102, each of the notches 118 is generally aligned with a corresponding post 120. The posts 120 and notches 118 generally assist in holding the cartridge 100 in place over the indexing mechanism 121 so that the cartridge 100 may be rotated and indexed prior to testing. The posts 120 and notches 118 also assist in aligning a test-sensor cavity 114 with an ejection mechanism and a test-sensor dispensing port 122 so that a test sensor 112 may be ejected for testing.

Once the test sensor 112 is aligned with the test-sensor dispensing port 122 prior to testing, an ejection mechanism, which may include a knife or a blade, may be moved in a lateral direction (i.e., in the direction of Arrow A) and may puncture a seal at a first end of the test-sensor cavity 114. The ejection mechanism then engages the test sensor 112, pushing the test sensor 112 in the direction of Arrow A. The test sensor 112 then may puncture and burst through a seal at the opposite end of the test-sensor cavity 114. The test sensor 112 is then excised out of the test-sensor dispensing port 122 into a read position, where the test sensor 112 is aligned with electrical contacts of the meter 102 and an analyte test may be performed.

Various types of meters and/or generations of meters may include different amounts and/or configurations of posts. FIGS. 3a-d illustrate representative views of non-limiting examples of indexing mechanisms 200, 220, 240, 260. Each indexing mechanism 200, 220, 240, 260 has a different number of posts 202, 222, 242, 262 respectively. The indexing mechanism 200 of FIG. 3a includes five uniformly-spaced posts 202. The indexing mechanism 220 of FIG. 3b includes ten uniformly-spaced posts 222. The indexing mechanism 240 of FIG. 3c includes two uniformly-spaced posts 242. The indexing mechanism 260 of FIG. 3d includes five notches 362 that are uniformly-spaced over a portion (e.g., about half) of the periphery of the indexing mechanism 260. It is contemplated that an indexing mechanism may include a different number of posts than those of the embodiments of FIGS. 3a-c. It is further contemplated that the posts may be positioned along the indexing mechanism in ways other than those shown in the illustrated embodiments. For example, the posts may be spaced non-uniformly along the periphery or other portions of the indexing mechanism or a portion thereof.

According to the present invention, the use of an incompatible test-sensor cartridge is inhibited or prevented by varying the amount and/or position of openings on the test-sensor cartridge. The amount and/or position of the openings may be determined based on (1) the amount and positions of the projections of a meter(s) with which the test sensors are compatible and (2) the amount and positions of the projections of a meter(s) with which the test sensors are not compatible. Thus, the openings of the test-sensor cartridge are adapted to receive all of the projections of a compatible meter(s), while at least one projection of an incompatible meter(s) does not fit within the openings of the test-sensor cartridge. By varying the number and/or position of the openings of a test-sensor cartridge such that at least one projection of the meter does not fit within the openings of an incompatible meter, the cartridge is inhibited or prevented from fitting within the meter. Thus, a user could readily determine that that a particular test-sensor cartridge should not be used with that particular meter.

Figure 4A:
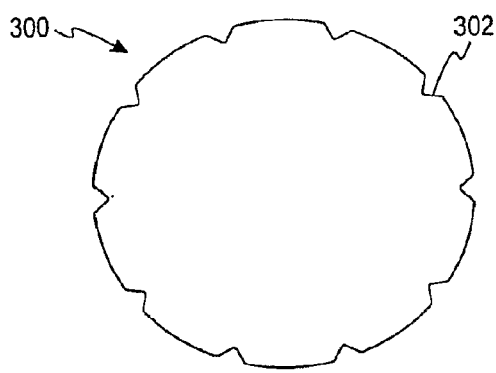
FIG. 4a illustrates a top, representative view of a test-sensor cartridge according to one embodiment.
Figure 4B:
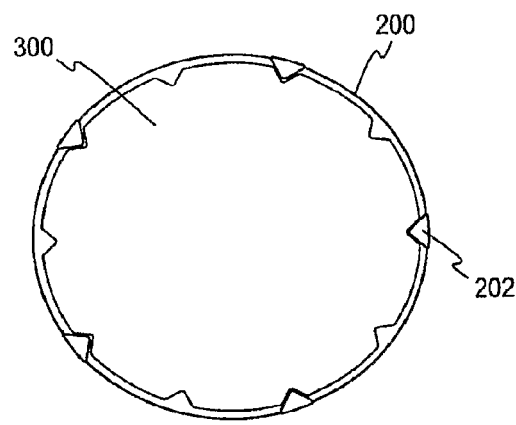
FIGS. 4b-e illustrate top, representative views of the test-sensor cartridge of FIG. 4a being used in connection with the indexing mechanisms of FIGS. 3a-c.
Figure 4C:
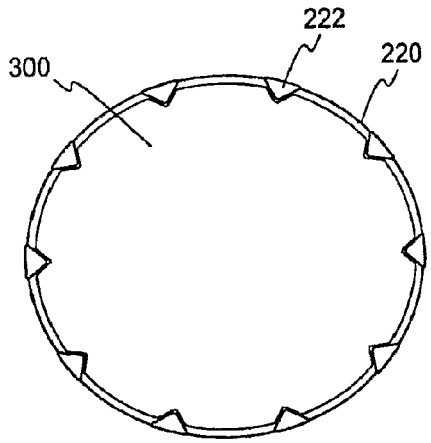
Figure 4D:
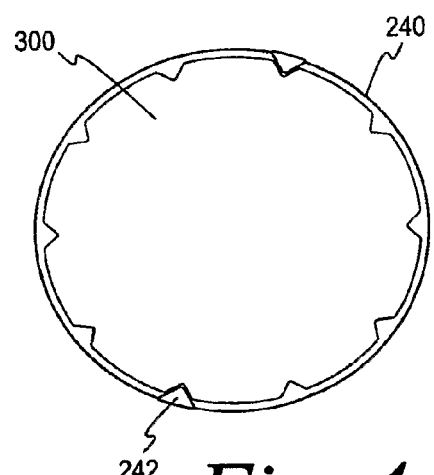
Figure 4E:
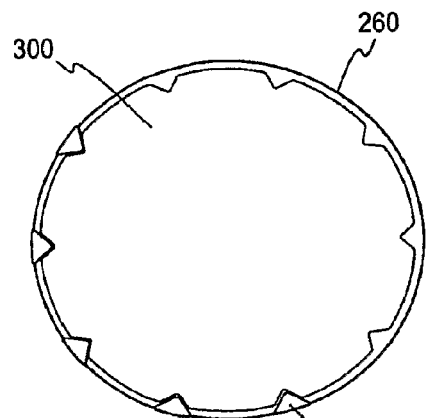

Referring to FIG. 4a, for example, a representative view of a cartridge 300 having ten uniformly-spaced notches 302 is shown. FIGS. 4b-e illustrate the cartridge 300 being used in connection with the indexing mechanisms 200, 220, 240, 260 of FIGS. 3a-d, respectively. The number and configuration of the notches 302 of the cartridge 300 are such that all of the posts 202, 222, 242, 262 of the various indexing mechanisms 200, 220, 240, 260 may fit within a corresponding one of the notches 302. Thus, the cartridge 300 would fit within a meter having the indexing mechanisms 200, 220, 240, 260 of FIGS. 3a-c, thereby indicating that the test sensors of the cartridge 300 are compatible with each of the corresponding meters.

Figure 5A:
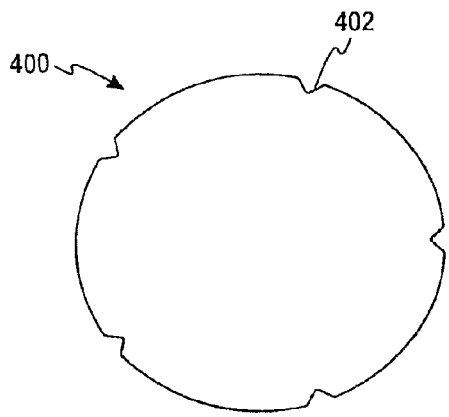
FIG. 5a illustrates a top, representative view of a test-sensor cartridge according to another embodiment.
Figure 5B:
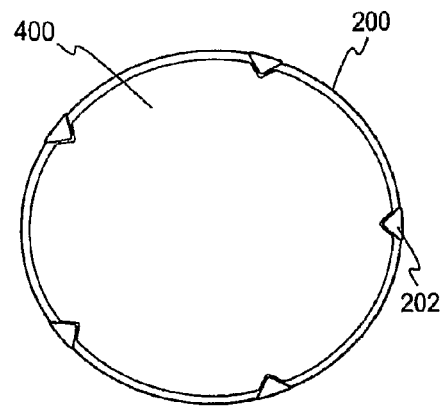
FIGS. 5b-e illustrate top, representative views of the test-sensor cartridge of FIG. 5a being used in connection with the indexing mechanisms of FIGS. 3a-c.
Figure 5C:
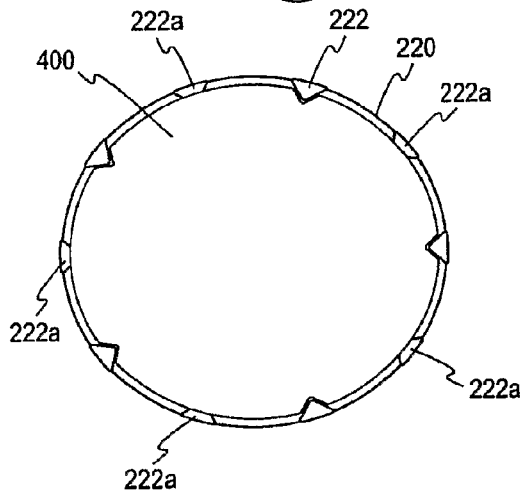
Figure 5D:
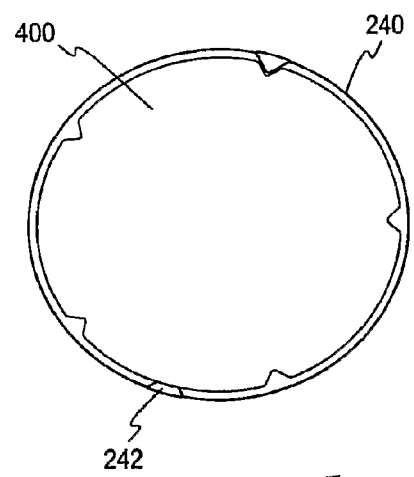
Figure 5E:
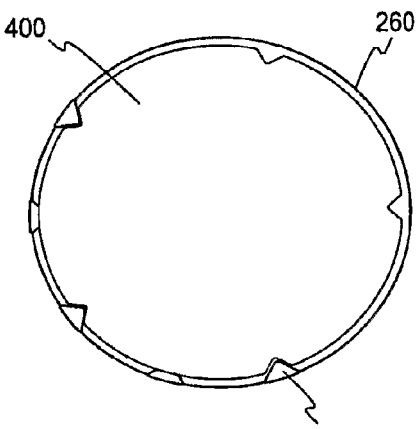

Referring now to FIG. 5a, a representative view of a cartridge 400 having five uniformly-spaced notches 402 is shown. FIGS. 5b-e illustrate the cartridge 400 being used in connection with the indexing mechanisms 200, 220, 240, 260 of FIGS. 3a-d, respectively. Referring to FIG. 5b, the cartridge 400 fits within the indexing mechanism 220, which includes a corresponding five posts 202 positioned uniformly on the periphery of the indexing mechanism 200. As shown in FIGS. 5*c-e*, however, the cartridge 400 does not fit within the indexing mechanisms 220, 240, and 260 of FIG. 3*b-d*, respectively. Referring to FIG. 5*c*, the indexing mechanism 220 includes more posts 222 (ten) than there are notches 402 (five) in the cartridge 400. Thus, five of the ten posts 222 (i.e., every other post 222*a*) collide with the surface 103 of the cartridge 400, thus indicating to a user that the cartridge 400 is not compatible with a meter including the indexing mechanism 220. As shown in FIG. 5*d*, one of the two posts 242 of the indexing mechanism 240 of FIGS. 3*c* does not fit within the notches 402 of the cartridge 402. Similarly, as depicted in FIG. 5*e*, a maximum of three of the five posts 262 of the indexing mechanism 260 fit within the notches 402. Although in FIGS. 5*d-e*, the number of notches 402 is greater than or the same as the number of posts 242, 262, respectively, at least one of the posts 242, 262 is not aligned with at least one of the notches 402, thus indicating to the user that the cartridge 400 is incompatible with a meter having the corresponding indexing mechanism 240, 260.

Although the notches 302, 402 of the illustrated embodiments are uniformly-spaced along the periphery of the respective cartridges, 300, 400, it is contemplated that a cartridge of the present invention may have notches or other openings arranged in other positions. For example, the notches or other openings may be positioned along only a portion of the periphery of the cartridge, positioned non-uniformly over the periphery of the cartridge, positioned uniformly or non-uniformly on the flat surface of the cartridge (e.g., not on the periphery), combinations thereof, or the like. Furthermore, it is contemplated that a different number of openings and/or projections may be used including, for example, a single opening and/or projection.

Figure 6:
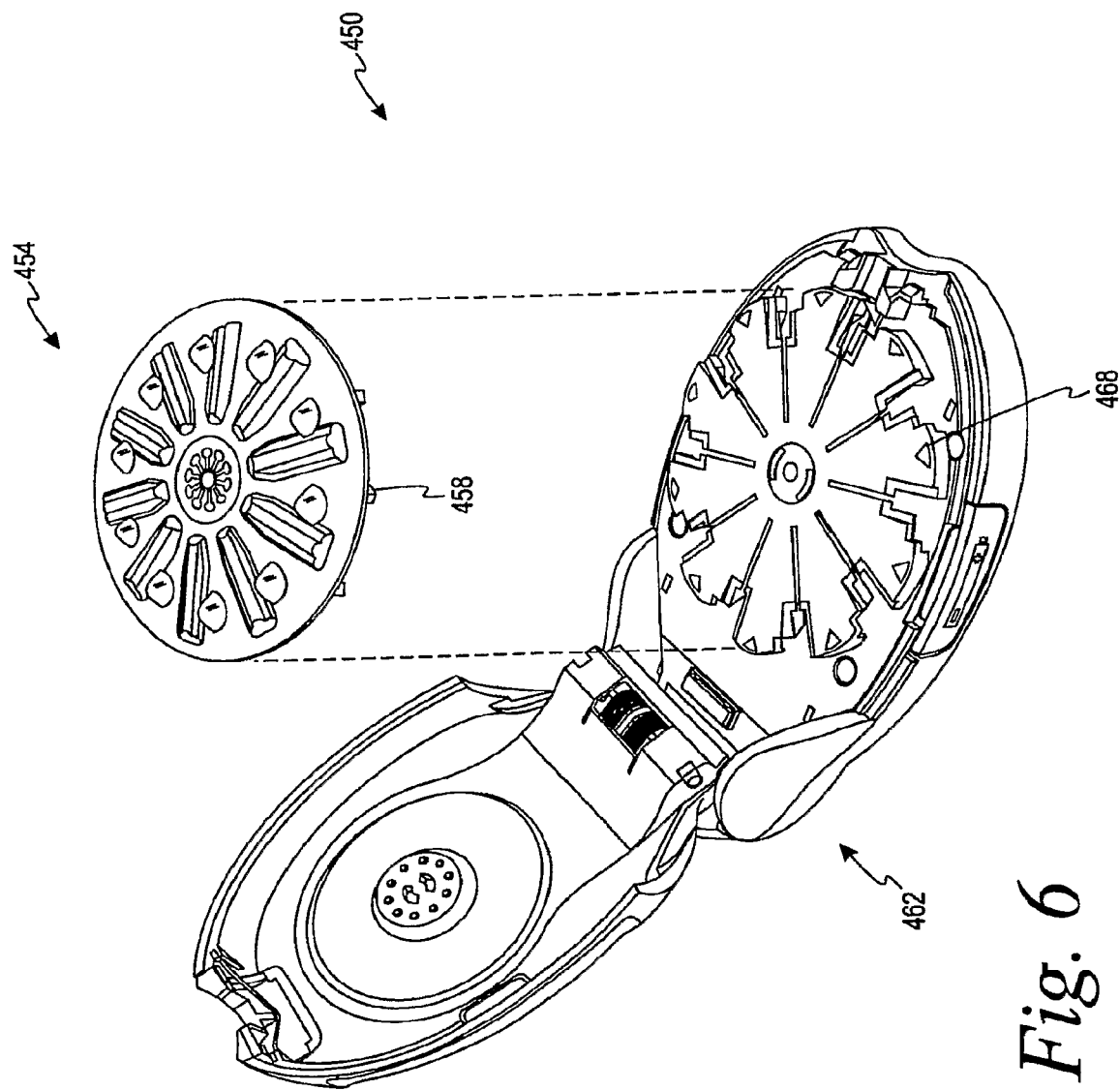
FIG. 6 is a perspective view of a sensor-dispensing instrument or meter in an open position showing a test-sensor cartridge being inserted according to another embodiment.

The concepts of the present invention may also be applied to a meter/cartridge assembly where a component of the meter (e.g., an indexing mechanism within the meter) includes openings and the test-sensor cartridge includes projections adapted to mate with at least one of the openings. One example of such a meter/cartridge assembly 450 is illustrated in FIG. 6. The meter/cartridge assembly 450 includes a test-sensor cartridge 454 having projections 458. It is contemplated that the projections 458 may have other locations, shapes, combinations thereof, or the like. The meter/cartridge assembly 450 also includes a meter 462 having openings 468 positioned on an indexing mechanism 472. It is contemplated that the openings 468 may have other locations, forms, combinations thereof, or the like. The cartridge projections 458 are arranged such that the openings of a compatible meter are adapted to receive all of the projections 458 of the cartridge 454. The openings of an incompatible meter are adapted to receive at least one but less than all of the projections 458 of the cartridge 454, thus indicating to a user that the cartridge 454 is incompatible with the meter.

Figure 7A:
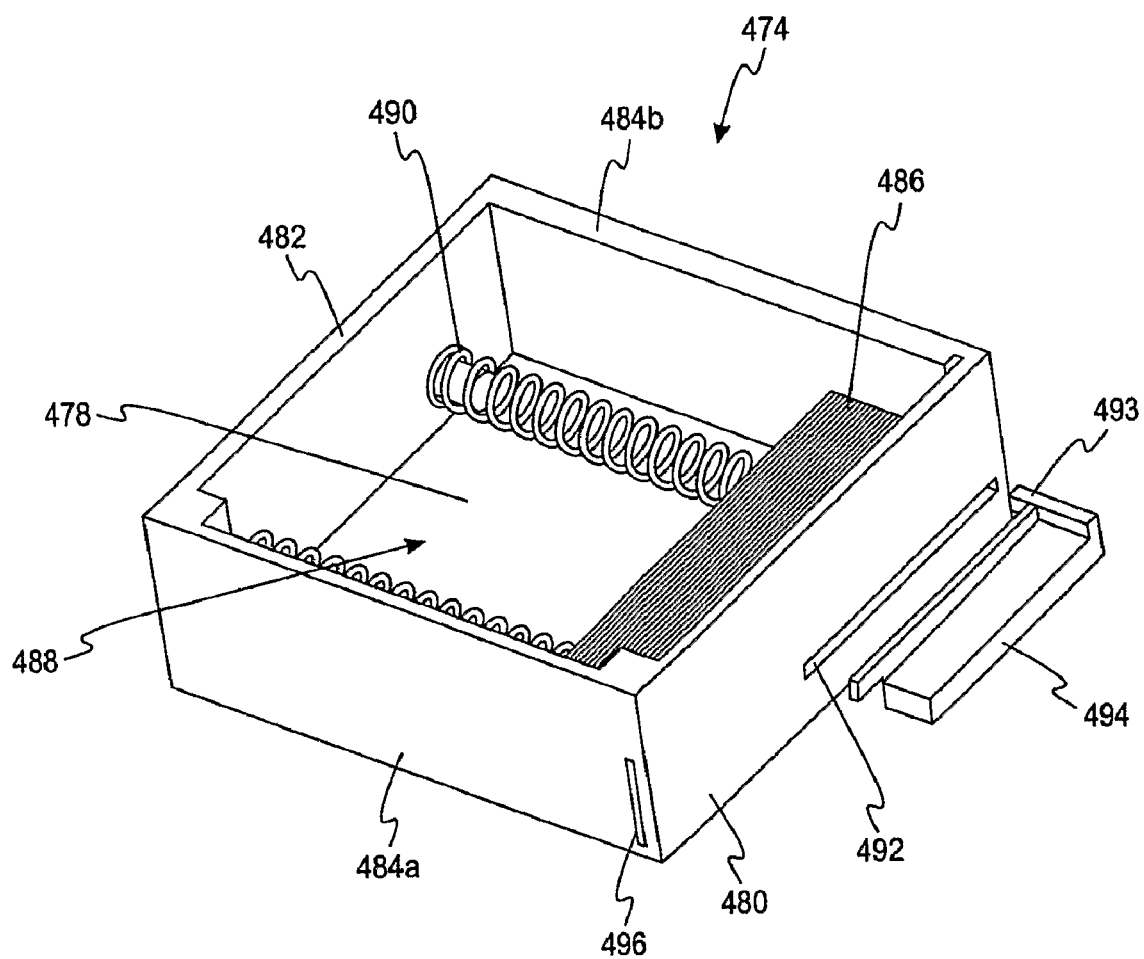
FIG. 7a is a perspective internal view of a stacked test-sensor cartridge and an ejection mechanism according to one embodiment.

The present invention may also be applied to inhibit or prevent a stacked test-sensor cartridge from being used with an incompatible sensor-dispensing instrument. Referring to FIGS. 7*a,b*, for example, a stacked test-sensor cartridge 474 includes a base 478, a front wall 480, a rear wall 482, opposing side walls 484*a*, 484*b*, and a cover (not shown). The cartridge 474 is adapted to receive a plurality of stacked test-sensors 486 within a central cavity 488 created by the sidewalls 484*a*, 484*b*, the front wall 480, and the rear wall 478 and between the base 478 and the top cover. The test-sensor cartridge 474 further includes a test-sensor retention mechanism 490 (e.g., a spring) to ensure that the test sensors 486 remain in contact with each other and flush with an interior face of the front wall 480. The front wall 480 generally includes an opening 492 adapted to allow at least a projection 493 of an ejection mechanism 494 of the meter 476 to be inserted through the opening 492. The ejection mechanism 494 may then engage a test sensor 486 such that the test sensor 486 may be ejected through a slot 496 in the cartridge 474 and a slot 498 of the meter 476 that is generally aligned with the slot 496 of the cartridge 474.

According to the present invention, the opening 492 is positioned and/or sized to receive an ejection mechanism 494 of a meter that is compatible with the test-sensor cartridge 474. The opening 492 is also positioned and/or sized so that an ejection mechanism 494 of an incompatible meter may not fit within the opening 492. Thus, when a user attempts to eject a test sensor 486 from a cartridge that is incompatible with the meter, the ejection mechanism of an incompatible meter will not engage the test sensor. The test sensor, therefore, will not be ejected, thus indicating to the user that the test-sensor cartridge 474 is not compatible with the particular meter.

It is contemplated that other features of the stacked test-sensor cartridge may also be positioned, sized, shaped, combinations thereof, or the like to limit the interchangeability of the cartridge between various types and/or generations of meters. For example, the dimensions and/or shape of the base 478, the front wall 480, the rear wall 482, the side walls 484*a*, 484*b*, the cover, or combinations thereof may be sized and/or shaped so that the cartridge 474 may only fit within a compatible meter(s). Alternatively or additionally, the slot 496 may be sized, shaped, and/or positioned to limit the use of the cartridge 474 with incompatible meters. For example, the slot 496 may be positioned such that the slot 496 does not align with a slot (e.g., slot 498 of FIG. 7*b*) of an incompatible meter. It is contemplated that the size, shape, position, combinations thereof, or the like of other components of the cartridge 474 may also be varied accordingly. It is also contemplated that other stacked test-sensor cartridges may also be used with the present invention.

As an alternative or in addition to mismatching the number and/or position of the openings of a test-sensor cartridge, the location of the openings relative to the test sensors and corresponding test-sensor cavities may be shifted. Because the openings assist in positioning and aligning a test sensor and a corresponding test-sensor cavity with an ejection mechanism and the sensor-dispensing port of a meter, shifting the openings makes it unlikely that the ejection mechanism will engage and eject a test sensor. This may serve as an additional or an alternative indication to a user that the test-sensor cartridge is incompatible with the meter.

Figure 8:
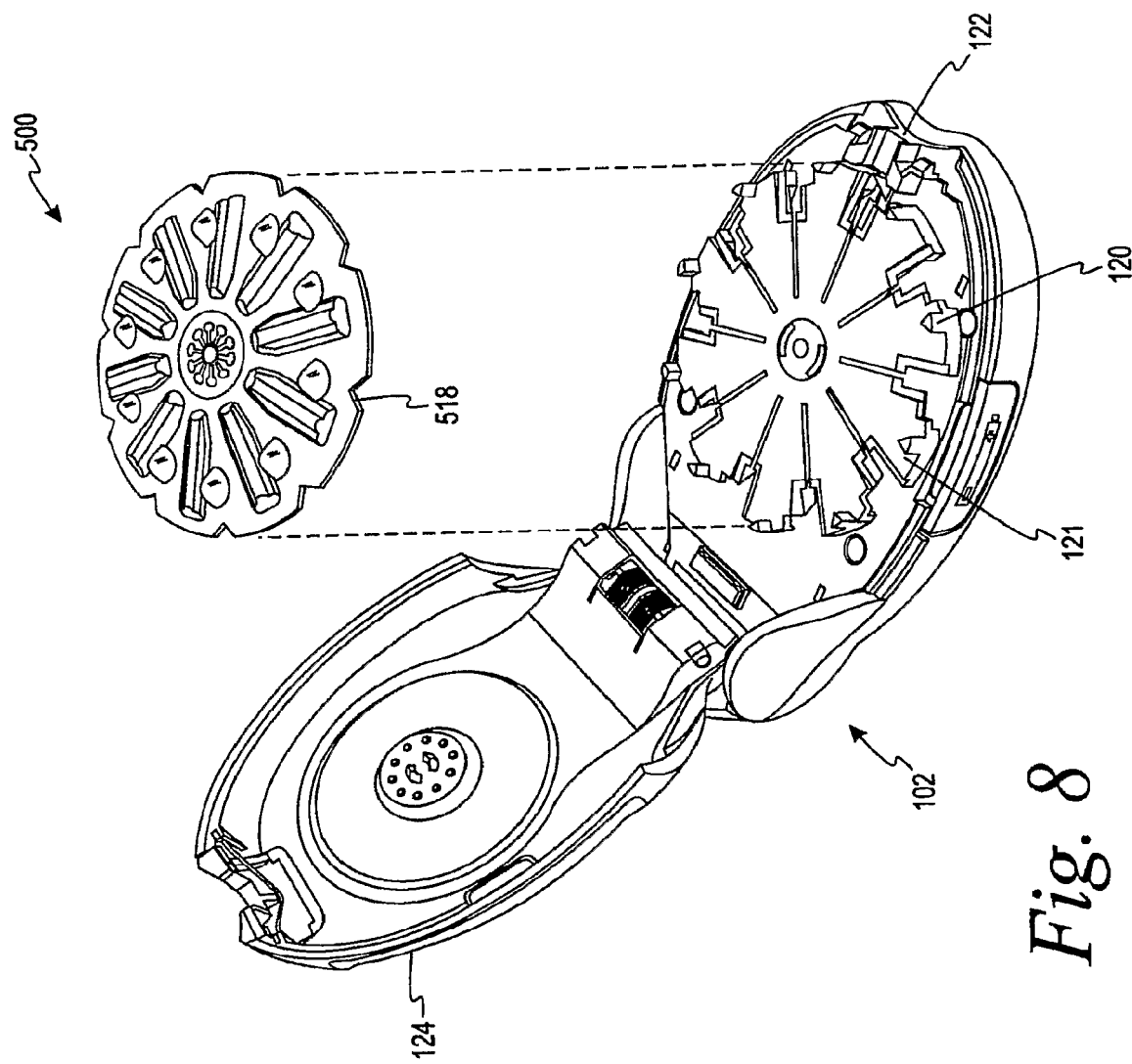
FIG. 8 is a perspective view of a sensor-dispensing instrument or meter in an open position showing a test-sensor cartridge being inserted according to yet another embodiment.

An example of shifting the location of the openings of a test-sensor cartridge relative to the location of test sensors and test-sensor cavities of the cartridge is illustrated in FIG. 8. FIG. 8 shows the meter 102 of FIG. 2 being used in connection with a cartridge 500. The cartridge 500 includes a plurality of notches 518 and is generally similar to the cartridge 100 of FIG. 2. The locations of the notches 518 of the cartridge 500, however, have been shifted slightly from the locations of the notches 118 of the cartridge 100 of FIG. 2. Because the meter 102 is configured for use with a cartridge (e.g., the cartridge 100) having notches positioned a certain distance relative to the test sensors and test-sensor cavities, shifting the notches relative to the test-sensors and test-sensor cavities makes it unlikely that the ejection mechanism will engage and eject a test sensor. Thus, applying this concept to the cartridges of FIGS. 5*c-e*, even if the cartridge 400 is somehow forced into a meter having the indexing mechanisms 220, 240, 260, the ejection mechanism of the corresponding meters would be unlikely to engage and eject a test-sensor.

While the invention is susceptible to various modifications and alternative forms, specific embodiments and methods thereof have been shown by way of example in the drawings and are described in detail herein. It should be understood, however, that is not intended to limit the invention to the particular forms or method disclosed, but, to the contrary, the intention is to cover all modifications, equivalents, and alternatives falling within the spirit and scope of the invention.

Alternative Embodiment A

A test-sensor cartridge comprising:
a plurality of test sensors adapted to assist in determining an analyte concentration of a fluid sample;
a plurality of walls forming at least one cavity therein, the at least one cavity being adapted to contain the plurality of test sensors; and
at least one opening formed on a surface of the cartridge,
wherein the at least one opening is adapted to receive each of at least one projection of a first sensor-dispensing instrument with which the cartridge is compatible, and
wherein the at least one opening is adapted to receive at least one but less than all of at least one projection of a second sensor-dispensing instrument with which the cartridge is incompatible.

Alternative Embodiment B

The cartridge of Alternative Embodiment A, wherein the plurality of test sensors is electrochemical test sensors.

Alternative Embodiment C

The cartridge of Alternative Embodiment A, wherein the test-sensor cartridge is a blister-pack type cartridge.

Alternative Embodiment D

The cartridge of Alternative Embodiment C, wherein the at least one opening is a plurality of openings.

Alternative Embodiment E

The cartridge of Alternative Embodiment D, wherein the plurality of openings is a plurality of notches.

Alternative Embodiment F

The cartridge of Alternative Embodiment D, wherein the plurality of openings is uniformly-spaced.

Alternative Embodiment G

The cartridge of Alternative Embodiment D, wherein the plurality of openings is non-uniformly-spaced.

Alternative Embodiment H

The cartridge of Alternative Embodiment C, wherein the amount of the at least one projection of the first sensor-dispensing instrument is the same as or less than the amount of the at least one opening.

Alternative Embodiment I

The cartridge of Alternative Embodiment C, wherein the amount of the at least one projection of the second sensor-dispensing instrument is greater than the amount of the at least one opening.

Alternative Embodiment J

The cartridge of Alternative Embodiment. C, wherein the at least one opening is positioned such that the at least one cavity does not align with an ejection mechanism of the second sensor-dispensing instrument when the cartridge is in an indexed position in the second sensor-dispensing instrument.

Alternative Embodiment K

The cartridge of Alternative Embodiment C, wherein the at least one opening is positioned such that the at least one cavity does not align with a sensor-dispensing port of the second sensor-dispensing instrument when the cartridge is in an indexed position in the sensor-dispensing instrument.

Alternative Embodiment L

The cartridge of Alternative Embodiment A, wherein each of the at least one projection of the first sensor-dispensing instrument generally aligns with a corresponding at least one opening.

Alternative Embodiment M

The cartridge of Alternative Embodiment A, wherein at least one but less than all of the at least one projection of the second sensor-dispensing instrument generally aligns with a corresponding at least one opening.

Alternative Embodiment N

The cartridge of Alternative Embodiment A, wherein the test-sensor cartridge is a stacked test-sensor cartridge.

Alternative Embodiment O

The cartridge of Alternative Embodiment N, wherein the projection is positioned on an ejection mechanism.

Alternative Embodiment P

A test-sensor cartridge comprising:
a plurality of test sensors adapted to assist in determining an analyte concentration of a fluid sample;
a plurality of walls forming at least one cavity therein, the at least one cavity being adapted to contain the plurality of test sensors; and
at least one projection formed on a surface of the cartridge,
wherein each of the at least one projection is adapted to be received by at least one opening of a first sensor-dispensing instrument with which the cartridge is compatible, and wherein at least one but less than all of the at least one projection is adapted to be received by at least one opening of a second sensor-dispensing instrument with which the cartridge is incompatible.

Alternative Embodiment Q

The cartridge of Alternative Embodiment P, wherein the plurality of test sensors is electrochemical test sensors.

Alternative Embodiment R

The cartridge of Alternative Embodiment P, wherein the test-sensor cartridge is a blister-pack type cartridge.

Alternative Embodiment S

The cartridge of Alternative Embodiment R, wherein the at least one opening is a plurality of openings.

Alternative Embodiment T

The cartridge of Alternative Embodiment S, wherein the plurality of openings is a plurality of notches.

Alternative Embodiment U

The cartridge of Alternative Embodiment S, wherein the plurality of openings is uniformly-spaced.

Alternative Embodiment V

The cartridge of Alternative Embodiment S, wherein the plurality of openings is non-uniformly-spaced.

Alternative Embodiment W

The cartridge of Alternative Embodiment R, wherein the amount of the at least one opening of the first sensor-dispensing instrument is the same as or less than the amount of the at least one projection.

Alternative Embodiment X

The cartridge of Alternative Embodiment R, wherein the amount of the at least one opening of the second sensor-dispensing instrument is greater than the amount of the at least one projection.

Alternative Embodiment Y

The cartridge of Alternative Embodiment R, wherein the at least one projection is positioned such that the at least one cavity does not align with an ejection mechanism of the second sensor-dispensing instrument when the cartridge is in an indexed position in the second sensor-dispensing instrument.

Alternative Embodiment Z

The cartridge of Alternative Embodiment R, wherein the at least one projection is positioned such that the at least one cavity does not align with a sensor-dispensing port of the second sensor-dispensing instrument when the cartridge is in an indexed position in the sensor-dispensing instrument.

Alternative Embodiment AA

The cartridge of Alternative Embodiment P, wherein the at least one projection generally aligns with a corresponding at least one opening of the first sensor-dispensing instrument.

Alternative Embodiment AB

The cartridge of Alternative Embodiment P, wherein the at least one projection generally aligns with at least one but less than all of the at least one opening of the second sensor-dispensing instrument.

Alternative Embodiment AC

A method of determining whether a test-sensor cartridge is compatible with a sensor-dispensing instrument, the method comprising the acts of:
providing a test-sensor cartridge including a plurality of walls forming at least one cavity therein, the at least one cavity being adapted to contain a plurality of test sensors, the plurality of test sensors being adapted to assist in the determination of a concentration of an analyte in a fluid sample, the test-sensor cartridge having at least one opening formed on at least one of the plurality of walls;
providing a sensor-dispensing instrument having at least one projection located therein;
inserting the test-sensor cartridge into the sensor-dispensing instrument; and
determining whether the test-sensor cartridge is compatible with the sensor-dispensing instrument based on whether the at least one opening is adapted to receive each of the at least one projection.

Alternative Embodiment AD

The method of Alternative Embodiment AC, wherein the plurality of test sensors is electrochemical test sensors.

Alternative Embodiment AE

The method of Alternative Embodiment AC, wherein the test-sensor cartridge is a blister-pack type cartridge.

Alternative Embodiment AF

The method of Alternative Embodiment AE, wherein the at least one opening is at least one notch.

Alternative Embodiment AG

The method of Alternative Embodiment AE, wherein the at least one opening is a plurality of openings.

Alternative Embodiment AH

The method of Alternative Embodiment AG, wherein the plurality of openings is uniformly-spaced.

Alternative Embodiment AI

The method of Alternative Embodiment AG, wherein the plurality of openings is non-uniformly-spaced.

Alternative Embodiment AJ

The method of Alternative Embodiment AF, wherein the at least one projection is a plurality of projections.

Alternative Embodiment AK

The method of Alternative Embodiment AJ, wherein the plurality of projections is uniformly-spaced along a periphery of an indexing mechanism.

Alternative Embodiment AL

The method of Alternative Embodiment AC, wherein if the amount of the at least one opening is less than the amount of the at least one projection, the sensor-dispensing instrument is incompatible with the test-sensor cartridge.

Alternative Embodiment AM

The method of Alternative Embodiment AC, wherein the test-sensor cartridge is a stacked test-sensor cartridge.

Alternative Embodiment AN

The method of Alternative Embodiment AM, wherein the at least one projection is positioned on an ejection mechanism.

Alternative Embodiment AO

The method of Alternative Embodiment AC, wherein, if each of the at least one projection may be received by a corresponding at least one opening, the sensor-dispensing instrument is compatible with the test-sensor cartridge, and wherein, if at least one projection may not be received by the at least one opening, the sensor-dispensing instrument is incompatible with the test-sensor cartridge.

Alternative Embodiment AP

A method of determining whether a test-sensor cartridge is compatible with a sensor-dispensing instrument, the method comprising the acts of:
providing a test-sensor cartridge including a plurality of walls forming at least one cavity therein, the at least one cavity being adapted to contain a plurality of test sensors, the plurality of test sensors being adapted to assist in the determination of a concentration of an analyte in a fluid sample, the test-sensor cartridge having at least one projection formed on at least one of the plurality of walls;
providing a sensor-dispensing instrument having at least one opening located therein;
inserting the test-sensor cartridge into the sensor-dispensing instrument; and
determining whether the test-sensor cartridge is compatible with the sensor-dispensing instrument based on whether the at least one opening is adapted to receive each of the at least one projection.

Alternative Embodiment AQ

The method of Alternative Embodiment AP, wherein the plurality of test sensors is electrochemical test sensors.

Alternative Embodiment AR

The method of Alternative Embodiment AP, wherein the test-sensor cartridge is a blister-pack type cartridge.

Alternative Embodiment AS

The method of Alternative Embodiment AR, wherein the at least one opening is at least one notch.

Alternative Embodiment AT

The method of Alternative Embodiment AR, wherein the at least one opening is a plurality of openings.

Alternative Embodiment AU

The method of Alternative Embodiment AT, wherein the plurality of openings is uniformly-spaced.

Alternative Embodiment AV

The method of Alternative Embodiment AT, wherein the plurality of openings is non-uniformly-spaced.

Alternative Embodiment AW

The method of Alternative Embodiment AR, wherein the at least one projection is a plurality of projections.

Alternative Embodiment AX

The method of Alternative Embodiment AW, wherein the plurality of projections is uniformly-spaced along a periphery of the at least one wall.

Alternative Embodiment AY

The method of Alternative Embodiment AQ, wherein if the amount of the at least one opening is less than the amount of the at least one projection, the sensor-dispensing instrument is incompatible with the test-sensor cartridge.

Alternative Embodiment AZ

The method of Alternative Embodiment AQ, wherein, if each of the at least one projection may be received by a corresponding at least one opening, the sensor-dispensing instrument is compatible with the test-sensor cartridge, and wherein, if at least one projection may not be received by the at least one opening, the sensor-dispensing instrument is incompatible with the test-sensor cartridge.

Alternative Embodiment BA

A test-sensor cartridge comprising:
a plurality of walls forming at least one cavity therein, the at least one cavity being adapted to contain a plurality of test sensors, the plurality of test sensors being adapted to assist in the determination of a concentration of an analyte in a fluid sample; and
at least one opening formed on a surface of the cartridge, the at least one opening assisting in indexing the test-sensor cartridge,
wherein when the test-sensor cartridge is indexed within a first sensor-dispensing instrument with which the cartridge is compatible, a test-sensor cavity is aligned with an ejection mechanism, and wherein when the test-sensor cartridge is indexed within a second sensor-dispensing instrument with which the cartridge is incompatible, a test-sensor cavity is not aligned with an ejection mechanism.

Alternative Embodiment BB

The cartridge of Alternative Embodiment BA, wherein the plurality of test sensors is electrochemical test sensors.

Alternative Embodiment BC

The cartridge of Alternative Embodiment BA, wherein the test-sensor cartridge is a blister-pack type cartridge.

Alternative Embodiment BD

The cartridge of Alternative Embodiment BC, wherein the at least one opening is a plurality of openings.

Alternative Embodiment BE

The cartridge of Alternative Embodiment BD, wherein the plurality of openings is a plurality of notches.

Alternative Embodiment BF

The cartridge of Alternative Embodiment BD, wherein the plurality of openings is uniformly-spaced along a periphery of the surface of the cartridge.

Alternative Embodiment BG

The cartridge of Alternative Embodiment BC, wherein the amount of the at least one projection of the first sensor-dispensing instrument is the same as or less than the amount of the at least one opening.

Alternative Embodiment BH

The cartridge of Alternative Embodiment BC, wherein the at least one opening is positioned such that the at least one cavity does not align with an ejection mechanism of the second sensor-dispensing instrument when the cartridge is in an indexed position in the second sensor-dispensing instrument.

Alternative Embodiment BI

The cartridge of Alternative Embodiment BC, wherein the at least one opening is positioned such that the at least one cavity does not align with a sensor-dispensing port of the second sensor-dispensing instrument when the cartridge is in an indexed position in the sensor-dispensing instrument.

Alternative Embodiment BJ

The cartridge of Alternative Embodiment BA, wherein the at least one opening generally aligns with a corresponding at least one projection of the first sensor-dispensing instrument.

The invention claimed is:

1. An analyte-testing system for determining an amount of an analyte in a fluid test sample, the system comprising:
    a test-sensor cartridge, the test-sensor cartridge including
        a plurality of test sensors adapted to be removed from the test-sensor cartridge;
        a plurality of walls forming at least one cavity therein, the at least one cavity being adapted to contain the plurality of test sensors, and
        at least one opening formed on a surface of the cartridge; and
    a first sensor-dispensing instrument having at least one projection,
    wherein, the at least one opening is adapted to receive each of the at least one projection of the first sensor-dispensing instrument, and
    wherein, the at least one opening is adapted to receive at least one but less than all of at least one projection of a second sensor-dispensing instrument with which the cartridge is incompatible.

2. The analyte-testing system of claim 1, wherein the test-sensor cartridge is a blister-pack type cartridge.

3. The analyte-testing system of claim 2, wherein the at least one opening is a plurality of openings.

4. The analyte-testing system of claim 3, wherein the plurality of openings is a plurality of notches.

5. The analyte-testing system of claim 3, wherein the plurality of openings is uniformly-spaced.

6. The analyte-testing system of claim 3, wherein the plurality of openings is non-uniformly-spaced.

7. The analyte-testing system of claim 1, wherein the amount of the at least one projection of the first sensor-dispensing instrument is the same as or less than the amount of the at least one opening.

8. The analyte-testing system of claim 1, wherein the amount of the at least one projection of the second sensor-dispensing instrument is greater than the amount of the at least one opening.

9. The analyte-testing system of claim 1, wherein the second sensor-dispensing instrument further comprises an ejection mechanism, wherein the at least one opening is positioned such that the at least one cavity is unaligned with the ejection mechanism of the second sensor-dispensing instrument when the cartridge is in an indexed position in the second sensor-dispensing instrument.

10. The analyte-testing system of claim 1, wherein the second sensor-dispensing instrument further comprises a sensor-dispensing port, wherein the at least one opening is positioned such that the at least one cavity is unaligned with the sensor-dispensing port of the second sensor-dispensing instrument when the cartridge is in an indexed position in the second sensor-dispensing instrument.

11. The analyte-testing system of claim 1, wherein each of the at least one projection of the first sensor-dispensing instrument generally aligns with a corresponding at least one opening.

12. The analyte-testing system of claim 1, wherein at least one but less than all of the at least one projection of the second sensor-dispensing instrument generally aligns with a corresponding at least one opening.

13. The analyte-testing system of claim 1, wherein the test-sensor cartridge is a stacked test-sensor cartridge.

14. An analyte-testing system for determining an amount of an analyte in a fluid test sample, the system comprising:
    a test-sensor cartridge, the test-sensor cartridge including
        a plurality of test sensors adapted to be removed from the test-sensor cartridge,
        a plurality of walls forming at least one cavity therein, the at least one cavity being adapted to contain the plurality of test sensors, and
        at least one projection formed on a surface of the cartridge; and a first sensor-dispensing instrument including at least one opening,
wherein each of the at least one projection is adapted to be received by the at least one opening of the first sensor-dispensing instrument, and
wherein at least one but less than all of the at least one projection is adapted to be received by at least one opening of a second sensor-dispensing instrument with which the cartridge is incompatible.

15. The analyte-testing system of claim 14, wherein the plurality of test sensors is electrochemical test sensors.

16. The analyte-testing system of claim 14, wherein the amount of the at least one opening of the first sensor-dispensing instrument is the same as or greater than the amount of the at least one projection.

17. The analyte-testing system of claim 14, wherein the amount of the at least one opening of the second sensor-dispensing instrument is less than the amount of the at least one projection.

18. A method of determining whether a test-sensor cartridge is compatible with a sensor-dispensing instrument, the method comprising the acts of:
   providing a test-sensor cartridge including a plurality of walls forming at least one cavity therein, the at least one cavity being adapted to contain a plurality of test sensors, the plurality of test sensors being adapted to assist in the determination of a concentration of an analyte in a fluid sample, the test-sensor cartridge having at least one opening formed on at least one of the plurality of walls;
   providing a sensor-dispensing instrument having at least one projection located therein;
   inserting the test-sensor cartridge into the sensor-dispensing instrument such that at least one opening of the test-sensor cartridge receives at least one projection of the sensor-dispensing instrument; and
   determining whether the test-sensor cartridge is compatible with the sensor-dispensing instrument based on whether the at least one opening is adapted to receive each of the at least one projection.

19. A method of determining whether a test-sensor cartridge is compatible with a sensor-dispensing instrument, the method comprising the acts of:
   providing a test-sensor cartridge including a plurality of walls forming at least one cavity therein, the at least one cavity being adapted to contain a plurality of test sensors, the plurality of test sensors being adapted to assist in the determination of a concentration of an analyte in a fluid sample, the test-sensor cartridge having at least one projection formed on at least one of the plurality of walls;
   providing a sensor-dispensing instrument having at least one opening located therein;
   inserting the test-sensor cartridge into the sensor-dispensing instrument such that at least one opening of the sensor-dispensing instrument receives at least one projection of the cartridge; and
   determining whether the test-sensor cartridge is compatible with the sensor-dispensing instrument based on whether the at least one opening is adapted to receive each of the at least one projection.

20. An analyte-testing system for determining an amount of an analyte in a fluid test sample, the system comprising:
   a test-sensor cartridge, the test-sensor cartridge including
      a plurality of walls forming at least one cavity therein, the at least one cavity being adapted to contain a plurality of test sensors, the plurality of test sensors being adapted to be removed from the test-sensor cartridge, and
      at least one opening formed on a surface of the cartridge, the at least one opening assisting in indexing the test-sensor cartridge; and
   a first sensor-dispensing instrument having an ejection mechanism,
   wherein one of the test-sensor cavities is aligned with the ejection mechanism when the test-sensor cartridge is indexed within the first sensor-dispensing instrument, and
   wherein one of the test-sensor cavities is not aligned with a second ejection mechanism of a second sensor-dispensing instrument when the test-sensor cartridge is indexed within the second sensor-dispensing instrument.

* * * * *